United States Patent [19]

Shields

[11] Patent Number: 5,558,649
[45] Date of Patent: Sep. 24, 1996

[54] CONICAL SYRINGE/NEEDLE SHIELD

[76] Inventor: Jack W. Shields, 1950 Las Tunas Rd., Santa Barbara, Calif. 93103

[21] Appl. No.: 377,929

[22] Filed: Jan. 25, 1995

[51] Int. Cl.$^6$ ................................. A61M 5/32
[52] U.S. Cl. .......................... 604/192; 604/263
[58] Field of Search .................. 604/192–198, 604/263, 110

[56] References Cited

U.S. PATENT DOCUMENTS

| | | |
|---|---|---|
| 3,008,570 | 11/1961 | Roehr et al. . |
| 3,110,309 | 12/1963 | Higgins . |
| 3,367,488 | 2/1968 | Hamilton . |
| 3,820,652 | 6/1974 | Thackston . |
| 3,878,846 | 4/1975 | Rimbaud . |
| 4,237,882 | 12/1980 | Wickham . |
| 4,334,536 | 6/1982 | Pfleger ............... 604/293 |
| 4,636,201 | 1/1987 | Ambrose et al. ....... 604/192 |
| 4,826,488 | 5/1989 | Nelson et al. ......... 604/192 |
| 4,872,552 | 10/1989 | Unger ................ 206/365 |
| 4,986,817 | 1/1991 | Code ................. 604/192 |
| 5,002,536 | 3/1991 | Thompson et al. ...... 604/192 |
| 5,021,049 | 6/1991 | Howard .............. 604/192 |
| 5,135,508 | 8/1992 | Vernamonti .......... 604/192 |
| 5,176,657 | 1/1993 | Shields . |
| 5,190,532 | 3/1993 | Yu .................. 604/192 |
| 5,304,148 | 4/1994 | Lannoye et al. ....... 604/192 |
| 5,334,173 | 8/1994 | Armstrong et al. ..... 604/263 |

FOREIGN PATENT DOCUMENTS 91-240423/33  2/1989  France .

OTHER PUBLICATIONS

Supplementary folder from Advances in Exposure Prevention 1994; 1:1–12.

*Primary Examiner*—John D. Yasko

[57] ABSTRACT

I describe a device comprising a hollow conical shield which wedge impacts the barrel of an inserted syringe having an affixed hollow needle initially covered by a needle scabbard, such that the hollow needle can be kept sterile after the needle scabbard is removed to fill the syringe; and such that accidental sticks are prevented after the syringe/needle is used to aspirate fluid from or inject a fluid into a subject.

3 Claims, 1 Drawing Sheet

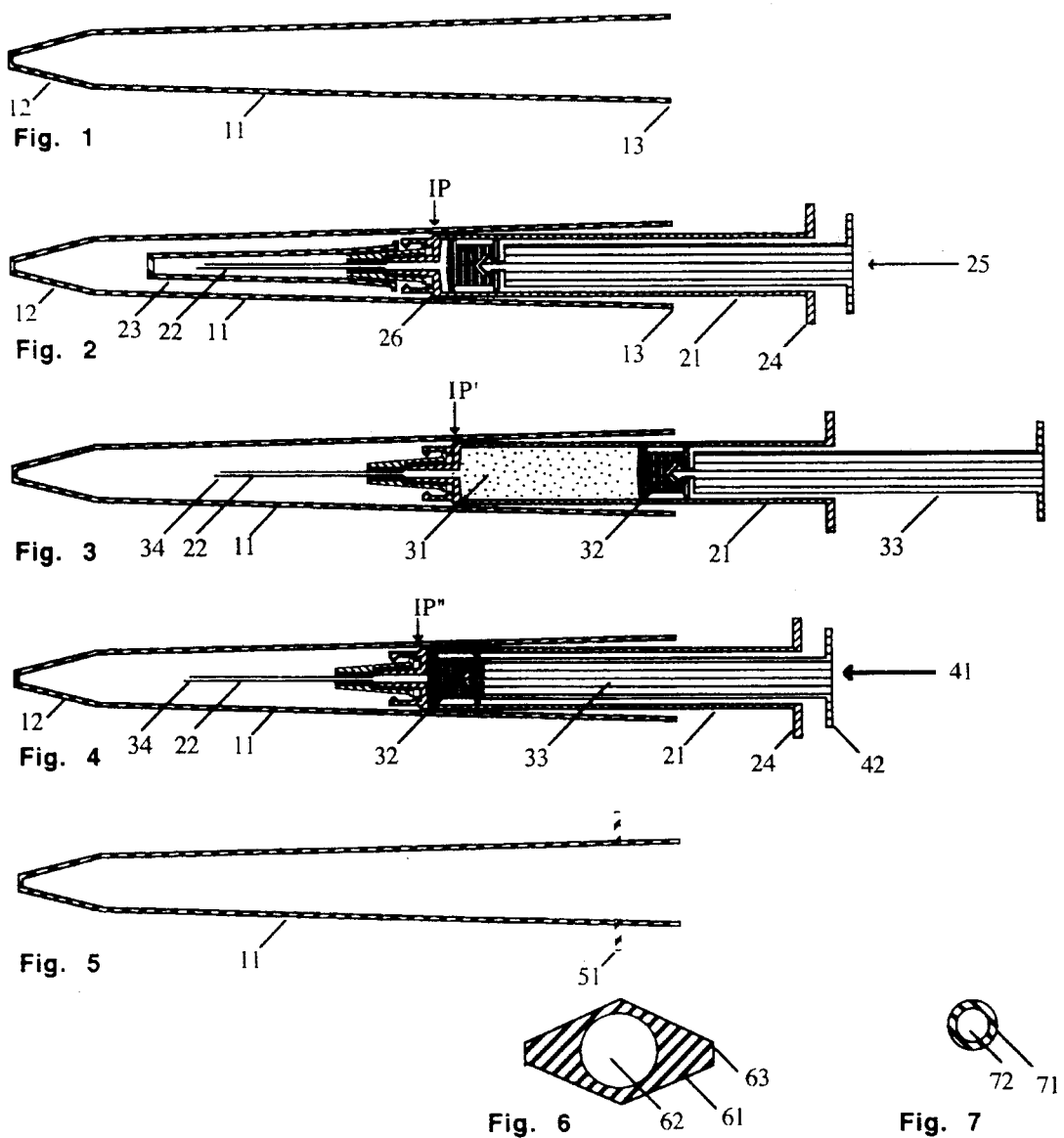

CONICAL SYRINGE/NEEDLE SHIELD

BACKGROUND OF THE INVENTION

1. Field of the Invention

This invention relates to the prevention of needle contamination with skin air- or skin-borne microorganisms before a filled syringe with an attached hollow-bore needle stick is used to give a fluid injection and the prevention of accidental needle stick injuries capable of transmitting blood-borne infections to health care workers, clean up personnel and bye-standers after use of syringe-attached needle for withdrawing a body fluid from or giving a fluid injection into a subject.

2. Prior Art

The use of disposable conical puncture-resistant needle-sheaths or scabbards for shielding sharp hollow-bore steel needles attachable to the leading ends of syringes has been standard practice for many years. The trailing ends of the sheaths or scabbards customarily attach to the leading end of a hub on a hollow-bore needle by means of a reversible conical slip-connection; while the trailing end of the needle hub attaches to the leading end of the syringe by means of a reversible Luer-slip or a Luer-Lok connection. Because accidental needle sticks after use of the hollow-bore needle attached to the syringe are common, it is now generally recommended that the syringe user not attempt to resheath the needle with its originally supplied scabbard, or to use a one-handed procedure wherein the needle is resheathed by reinsertion into the scabbard. The instant invention resembles a standard needle scabbard, but differs in that hollow conical shield is structured to wedge impact the leading end of an inserted cylindric syringe barrel in its mid-portion, instead of forming a slip connection in its trailing end with a leading cone on the needle hub.

The use of three-part puncture-resistant shields or shielding systems which cover the entire syringe or syringe with an attached needle, is also semi-standard procedure in accordance with U.S. patented disclosures by Roehr et al U.S. Pat. No. 3,008,570 (Nov. 14, 1961), Higgins U.S. Pat. No. 3,110,309 (Nov. 12, 1963); Hamilton U.S. Pat. No. 3,367,488 (Feb. 6, 1968), Thackston U.S. Pat. No. 3,820,652 (Jun. 28, 1974), Wickham U.S. Pat. No. 4,237,882 (Dec. 9, 1980) assigned to Sherwood Medical Industries, and Shields U.S. Pat. No. 5,176,657 (Jan. 5, 1993). The patent of Wickham is currently embodied in the Monoject® system wherein the syringe with or without an attached hollow needle is sold enclosed in a three part shielding system comprising a scabbard for the needle, a scabbard for the syringe and a trailing cap which seals the system. In this system, the needle hub slip connects inside the leading scabbard which, in turn, slip connects inside the leading end of the trailing scabbard to hold the syringe within, when the leading scabbard is tightly affixed to the leading end of the needle hub and the trailing end of the needle hub is slip-fit or locked onto the leading syringe end of the syringe. If the leading needle scabbard is removed or is not tightly slip-connected to the trailing scabbard, the inserted needle and needle-connected syringe will fall out with inversion of the trailing scabbard. This maneuver indicates that there is no frictional impaction between the leading end of the syringe and the leading end of the trailing scabbard, even though this scabbard shielding the syringe is made in the form of a cone whose leading end slopes sharply inward to stop the leading end of the syringe and tightly hold the conical part of a needle hub.

Shields ('657) disclosed a three part shielding system wherein the trailing scabbard is coned such that it wedge impacts the leading end of a reusable cylindric dental cartridge aspirating syringe, such that an inserted cartridge with an attached hollow needle, after use, can be ejected safely through the breech of the syringe by displacement of the leading scabbard in a trailing direction. The three part shielding system was claimed as useful for sterile containment of the cartridge before use, for safe holding the syringe/needle between uses, and safely ejecting the spent cartridge with attached needle after use. However, the system was not claimed as applicable to disposable syringes with attachable needles. The instant invention resembles said trailing scabbard, but differs in that the leading end is closed, instead of open to slip fit with the leading scabbard.

The use of a cylindric protective case which slides over a cylindric cartridge aspirating syringe to keep the contents of the cartridge sterile was described by Rimbaud in U.S. Pat. No. 3,878,846 (Apr. 22, 1975). In the French Patent #2654-629A (02.11.89), Floquet disclosed a single use syringe comprising a barrel and needle protected by a stepped cylindric outer casing into which the syringe barrel and needle are withdrawn and locked in once the syringe has been used. Currently, as described in *Advances in Exposure Prevention* 1994; 1: 1–12 with supplementary drawings, Sherwood Medical Corporation produces and sells a safety syringe, Monoject™, having a cylindric guard which slides forward over the barrel of a syringe and locks with twisting to protect the leading tip of the syringe-attached needle after use. Similarly, Becton-Dickinson Corporation produces and sells a safety syringe, B-D Safety-Lok™, having a protective cylindric sliding sleeve which can be pushed forward and locked in place to protect the leading tip of the needle after use. Because none of these sliding cylindric needle shielding mechanisms are claimed as cones which simply wedge impact the leading end of an inserted cylindric syringe, none are applicable to the instant invention.

The instant invention also differs from patents pending for other kinds of conical shields for needles or syringes, in that the leading end of cone is closed.

SUMMARY

The object of this invention is to provide health care workers with a simply operable and cost-efficient disposable shield to protect their patients from air- and finger-borne organisms potentially carried on hollow needles after a standard needle scabbard has been removed and a standard syringe/needle assembly is filled, but not yet used for giving an injection; and protect to health care workers, clean-up personnel and bye-standers from blood-borne infections caused by accidental needle sticks from sharp hollow-bore steel needles used to withdraw blood from patients or inject medications by means of standard needle/syringe assemblies. A unique feature of this simple conical shield is that, owing to dimensions and outer means for stabilization, the user will find that one-handed insertion of the syringe/needle assembly into the shield is extremely easy and safe.

BRIEF DESCRIPTION OF THE DRAWINGS

FIG. 1 is a mid-axial section of an empty conical syringe/needle shield. (Scale 1:1).

FIG. 2 is a mid-axial section of the conical shield containing an inserted 3 ml. Luer-Lok syringe with an affixed hollow covered by a needle scabbard.

FIG. 3 is a mid-axial section of the conical shield after the needle scabbard has been removed, the syringe has been partially filled, and the syringe/needle has been reinserted.

FIG. 4 is a mid-axial section of the conical shield after the syringe/needle have been used to discharge the syringe contents, and the syringe/needle has been wedge-impacted into the conical shield.

FIG. 5 is a mid-axial section of the hollow conical shield having an outside flange near the trailing end.

FIG. 6 is a cross section through a circumferential rhomboidal outside flange on the trailing end of the conical shield.

FIG. 7 is a cross section through a round external flange on the trailing end of a standard needle scabbard made to protect the leading end and shaft of a sharp hollow-bore steel needle hub-attached to the leading end of a standard Luer-Lok syringe.

DESCRIPTION OF THE PREFERRED EMBODIMENTS

A first preferred embodiment of this disposable hollow conical syringe/needle shield is shown in FIGS. 1–4.

FIG. 1 shows a conical shield 11 having a small closed leading end 12 and a large open trailing end 13. The conical shield is preferably made of a puncture-resistant, air-tight plastic material which is less rigid than the material from which a standard syringe is customarily fabricated.

FIG. 2 shows an empty standard 3 ml. Luer-Lok syringe 21 with an affixed hollow needle 22 and a conical needle scabbard 23 inserted into the conical shield 11 to an impaction point IP where the internal diameter of the conical shield 11 becomes less than the external diameter of the leading end of the cylindric barrel of the syringe 21. The distance between the point of impaction IP and the small closed leading end 12 of the conical shield 11 must be appreciably greater than distance between the impaction point IP and the leading end of the conical needle scabbard 23; while the internal diameter of the small closed leading end 12 must be appreciably greater than the external diameter of the needle scabbard 23 which reversibly sheaths the hollow needle 22. Moreover, the distance between the point of impaction IP and the large open trailing end 13 of the conical shield 11 must be more than half the length of the syringe barrel 21 and substantially less than the distance between the impaction point IP and the trailing flanges 24 on the Luer-Lok syringe 21. The internal slope of the conical shield 11 between the point of syringe impaction IP and the large open trailing end 13 must be very gradual with respect to the long axis of the conical shield 11 and the cylindric syringe barrel 21, so that maximal surface area will be in contact when the rigid cylindric syringe barrel 21 is inserted as far as possible into the less rigid conical shield 11 to create a tight wedge impaction whose tenacity will be proportional to the force exerted in the direction of the arrow 25.

With respect to the leading end of the conical shield 11 beyond the point of syringe barrel impaction IP, the Luer-Lok mechanism 26 in standard disposable syringes characteristically has an external diameter substantially less than that of the barrel and, therefore, does not become impacted when the cylindric syringe barrel 21 is inserted into the conical shield 11. As shown here, using a standard 3 ml. Luer-Lok syringe with an attached 1" hollow needle, substantial space resides between the internal surface of the conical shield and the Luer-Lok 26, the needle scabbard 23 and the hollow needle 22. Although a 1" hollow needle is illustrated, it should be noted that sufficient space remains in the leading confines of the hollow shield 11 to accommodate a 1.5" needle, along with its fitting conical needle scabbard.

FIG. 3 shows assembly of the conical shield 11 and syringe 21 after the needle scabbard has been removed and discarded and the syringe cylinder has been partially filled with fluid 31 through the hollow needle 22 by retraction of the piston 32 and attached plunger 33. The fluid-loaded syringe 21 has been inserted back into the confines of the conical shield 11 to a point of loose impaction IP'.

It should be noted that the conical shield 11, if sterilized and supplied as an assembly like that shown in FIG. 2, provides a sterile, as well as puncture-resistant environment to temporarily store and transport the loaded syringe 21 and affixed needle 22 until the contained fluid 31 is injected into a patient via the hollow needle 22 which is normally beveled and sharp on the leading end 34.

FIG. 4 shows re-assembly of the conical shield 11 and emptied syringe 21 after the fluid has been injected via the hollow needle 22 under the aegis of the piston 32 and plunger 33. Maximal manual force in the direction of the arrow 41 on the plunger thumb-ring 42, the trailing flange in the syringe 24, exposed cylindric syringe barrel 21, or tamping the closed narrow leading end 12 of the conical shield 11 against a firm surface in conjunction with the former manual maneuvers will cream a wedge impaction IP" of maximal tenacity between the leading end of the cylindric syringe barrel and the mid-portion of the conical shield.

When a tight wedge impaction is achieved, it will prove difficult to disrupt unless the user employs both hands to retract and twist exposed parts of the syringe simultaneously. Thus, after the syringe has been filled, the user may transport the syringe with an affixed needle safely. After the syringe has been emptied or used for aspirating a body fluid, re-shielding of the syringe/needle will prevent personal needle stick injuries, as well as accidental injuries to others with maximal efficiency, especially if the user personally oversees disposal into a sharps container when it is convenient.

FIGS. 5–6 show structural means for enabling the user to employ the conical shield with one hand for maximal efficiency, as well as user/patient friendliness. As indicated in FIG. 5, the conical shield 11 is supplied with a circumferential trailing flange 51. As shown in cross section in FIG. 6, a rhomboid configuration of the circumferential trailing flange 61 will prevent the conical shield 11 from rotating on a flat or uneven surface. The flange will tilt the trailing large open trailing end upward, so that the user can easily insert the leading hollow needle, followed by the leading end the cylindric barrel into a large aperture 62. For a standard 3 ml. syringe, the aperture will be approximately 12 mm. in diameter, which is 2.0 to 2.5 times the diameter and 4–5 times the area of that available in the trailing end of the needle scabbard originally supplied with the hollow needle. Moreover, the extended ends 63 of the rhomboidal flange will permit the user to grasp the flange effectively with one hand to initiate and effect adequate insertion of the syringe into the conical shield.

For comparative purposes, FIG. 7 shows a cross section through a round flange on the trailing end of a standard disposable needle scabbard which reversibly slip connects over the leading part of needle hub, as illustrated in FIG. 2. The external diameter of the round flange is customarily 8–9 mm.; while the internal diameter of the aperture for inserting the needle and leading portion of the needle hub is customarily 5.2 to 5.8 mm. The area of a perfect circle being proportional the square of the radius, comparison of FIGS.

6–7 will illustrate that the user has a target 4–5 times the size of that in the trailing end of the needle scabbard for inserting the needle attached to the leading end of the cylindric syringe barrel into the conical syringe/needle shield. Moreover, comparison of the length and internal configuration of the needle scabbard 23 with counterparts in the conical syringe/needle shield 11 illustrated in FIGS. 2–3, will reveal that the user of the latter is obliged to insert the syringe/needle approximately twice as far before wedge impaction proceeds sequentially at points IP', IP and IP". Thus, the user is provided with more accuracy when reinserting the syringe/needle into the conical syringe/needle 11, instead of into the conical needle scabbard 23, irrespective of which unassisted hand is used to do so.

While it might be desirable to actually tether this disposable conical shield to the syringe to prevent loss during manual operation of the syringe/needle for withdrawing body fluid or injecting a fluid medication, a tethered shield would encumber customary use of the syringe/needle, or prove very inconvenient. However, if the disposable conical shield is supplied with the syringe/needle in a tamper-proof sterile package, as illustrated without the package in FIG. 2, some advantages might be listed as follows:

1. The hollow conical shield will be supplied in a sterile condition, such that after the disposable scabbard is removed from the hollow needle in order to fill the syringe, the interior of the conical shield will remain sterile and provide a safe housing for transport of the filled syringe and affixed needle before use for injecting a fluid medication.
2. The syringe can be supplied inserted into the hollow conical shield, but without an attached needle, so that the user can attach a sterile needle of his/her choice by means of the needle scabbard which will be discarded after the needle is attached to the syringe. Subsequent usage will be the same as already described.
3. Being of substantial size compared with the disposable needle scabbard, the disposable hollow conical shield will not be lost easily. If lost, another unsterile similar shield can be used to protect the needle after use in a patient. Because this conical syringe/needle shield will accommodate any standard 3 ml. Luer-lock syringe having an external barrel diameter ranging from 10.26 to 10.69 min., such conical shields could be supplied as shown in FIGS. 1 and 5, either in a packaged sterile condition for use after the syringe has been filled with sterile fluid, or in an unpackaged unsterile condition for use after the needle has been employed for injecting a fluid into patient or aspirating a body fluid.
4. Being of a standard size and configuration, this disposable conical syringe/needle shield will not only protect standard syringe-attached needles of any gauge and length not exceeding 1.5", but also a variety of self-sheathing needles wherein there is any doubt concerning the capacity of the self-sheathing system to withstand straight-on impact in the long axis of the needle.

Finally, it should be appreciated by those skilled in the art that this one piece disposable conical needle/syringe shield can be varied in details, materials and usages without departing from the spirit of the invention. For instances:

Therefore, I claim:
1. A conical syringe/needle shield for reversibly and safely enclosing a syringe having a cylindric barrel with an attached needle, a reversibly attachable needle scabbard and a trailing flange on the cylindric barrel, said conical syringe/needle shield comprising a hollow cone with:
   a. a needle puncture-resistant consistency,
   b. a closed apex,
   c. an open frustum having a trailing internal diameter greater than the external diameter of the cylindric barrel of the syringe;
   d. a hollow body between said closed apex and said open frustum, said hollow body having:
      i. an axial length approximately equal to the combined axial length of the cylindric barrel of the syringe with the attached needle,
      ii. an apical internal diameter smaller than the external diameter of the cylindric barrel of the syringe and larger than the outside diameter of the needle scabbard, and
      iii. an internal diameter which gradually reduces in size from said frustal internal diameter to said apical internal diameter, such that insertion of the cylindric barrel of the syringe through said open frustum into said hollow body to the point where the external diameter the cylindric barrel of the syringe and the internal diameter of said hollow body become equal will create a wedge impaction which leaves the leading end of the barrel of the syringe with the attached needle having an affixed needle scabbard in a closed space longer and wider than the attached needle having the affixed needle scabbard, and which leaves said open frustum of said hollow cone in a position overlying the trailing end of the cylindric barrel of the syringe substantially ahead of the trailing flange on the cylindric barrel.

2. The conical syringe/needle shield, as in claim 1, wherein said hollow body has a circumferential external flange near said open frustum of said hollow cone for finger placement, said circumferential external flange having a rhomboid external shape to prevent rolling of said conical syringe/needle shield on a flat, inclined or an uneven surface.

3. The conical syringe/needle shield, as in claims 1 or 2, wherein said closed apex, said hollow body, said open frustum and said circumferential external flange are substantially identical and equally capable of wedge impacting an inserted solid sharp instrument having:
   a. a sharp leading end shorter and smaller than said closed apex of said hollow cone;
   b. a body with an axial length approximately equal to or greater than said axial length of said hollow cone, said body being of greatest external diameter larger than said apical internal diameter and smaller than said frustal internal diameter of said hollow cone; and
   c. trailing means for finger manipulation exposed after the sharp leading end of the solid instrument is inserted insofar as possible into said hollow body of said hollow cone.

* * * * *